United States Patent
Govari et al.

(10) Patent No.: US 11,642,172 B2
(45) Date of Patent: May 9, 2023

(54) SHOWING CATHETER IN BRAIN

(71) Applicant: BIOSENSE WEBSTER (ISRAEL) LTD., Yokneam (IL)

(72) Inventors: Assaf Govari, Haifa (IL); Vadim Gliner, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 1069 days.

(21) Appl. No.: 16/292,549

(22) Filed: Mar. 5, 2019

(65) Prior Publication Data
US 2020/0281661 A1  Sep. 10, 2020

(51) Int. Cl.
*A61B 34/20* (2016.01)
*G16H 15/00* (2018.01)
(Continued)

(52) U.S. Cl.
CPC .............. *A61B 34/20* (2016.02); *A61B 6/501* (2013.01); *G16H 15/00* (2018.01); *G16H 30/20* (2018.01);
(Continued)

(58) Field of Classification Search
CPC . A61B 34/20; A61B 6/501; A61B 2034/2051; A61B 2034/2065; A61B 2034/2072; A61B 2034/2074; A61B 5/066; A61B 5/283; A61B 5/6822; A61B 5/6852; A61B 5/6868; A61B 8/4254; A61B 2090/364; A61B 5/062; G16H 15/00;
(Continued)

(56) References Cited

U.S. PATENT DOCUMENTS

| | | | | |
|---|---|---|---|---|
| 4,893,627 A | * | 1/1990 | Kehayias | A61K 49/06 600/431 |
| 5,042,486 A | * | 8/1991 | Pfeiler | A61B 34/20 378/98.2 |

(Continued)

FOREIGN PATENT DOCUMENTS

WO    WO 96/05768    2/1996

OTHER PUBLICATIONS

European Examination Report for Application No. 20160942.7-1113, dated May 18, 2021.
(Continued)

*Primary Examiner* — Sanjay Cattungal
(74) *Attorney, Agent, or Firm* — Troutman Pepper Hamilton Sanders LLP

(57) ABSTRACT

In one embodiment a medical tracking system, including a catheter to be inserted into blood vessels of a body-part of a living subject, and including a flexible shaft having a deflectable distal end, and a location tracking transducer in the distal end configured to output a signal indicative of a location of the transducer, a tracking subsystem to track locations of the distal end over time responsively to the signal, a display, and processing circuitry to add the tracked locations of the distal end to a movement log, and render to the display an image of at least part of the body-part with a representation of a length of the shaft of the catheter in at least one blood vessel of the body-part, with respective positions along the length of the shaft being located in the image responsively to respective ones of the tracked locations from the movement log.

15 Claims, 10 Drawing Sheets

(51) Int. Cl.
*G16H 30/20* (2018.01)
*A61B 6/00* (2006.01)

(52) U.S. Cl.
CPC ............... *A61B 2034/2051* (2016.02); *A61B 2034/2065* (2016.02); *A61B 2034/2072* (2016.02); *A61B 2034/2074* (2016.02)

(58) Field of Classification Search
CPC .... G16H 30/20; A61F 7/123; A61M 25/0105; A61M 25/0127
See application file for complete search history.

(56) References Cited

U.S. PATENT DOCUMENTS

| | | | |
|---|---|---|---|
| 5,391,199 A | 2/1995 | Ben Haim | |
| 5,417,213 A * | 5/1995 | Prince | A61K 49/18 600/419 |
| 5,553,619 A * | 9/1996 | Prince | A61B 5/411 600/431 |
| 5,590,654 A * | 1/1997 | Prince | A61M 5/16827 324/309 |
| 5,687,208 A * | 11/1997 | Bae | G16H 20/17 378/8 |
| 5,713,358 A * | 2/1998 | Mistretta | G01R 33/5619 324/309 |
| 5,724,978 A * | 3/1998 | Tenhoff | A61B 8/4245 600/467 |
| 5,746,208 A * | 5/1998 | Prince | G01R 33/5601 600/419 |
| 5,762,065 A * | 6/1998 | Prince | A61K 49/18 600/419 |
| 5,771,308 A * | 6/1998 | Florent | G06T 7/12 382/130 |
| 5,792,056 A * | 8/1998 | Prince | A61K 49/18 324/309 |
| 5,924,987 A * | 7/1999 | Meaney | G01R 33/56383 324/306 |
| 6,015,545 A * | 1/2000 | Thomsen | A61K 49/18 426/74 |
| 6,167,297 A * | 12/2000 | Benaron | G01N 33/57434 977/869 |
| 6,219,572 B1 * | 4/2001 | Young | G01R 33/5601 600/431 |
| 6,231,834 B1 * | 5/2001 | Unger | B82Y 5/00 600/431 |
| 6,239,724 B1 | 5/2001 | Doron et al. | |
| 6,240,311 B1 * | 5/2001 | Prince | G01R 33/5635 324/309 |
| 6,246,901 B1 * | 6/2001 | Benaron | A61B 5/415 977/869 |
| 6,304,769 B1 * | 10/2001 | Arenson | A61B 5/06 604/528 |
| 6,332,089 B1 | 12/2001 | Acker et al. | |
| 6,370,417 B1 * | 4/2002 | Horbaschek | A61B 6/504 600/431 |
| 6,375,931 B2 * | 4/2002 | Østensen | A61K 49/223 977/928 |
| 6,380,732 B1 | 4/2002 | Gilboa | |
| 6,442,415 B1 * | 8/2002 | Bis | A61M 25/0068 600/420 |
| 6,463,317 B1 * | 10/2002 | Kucharczyk | A61B 5/055 606/194 |
| 6,463,318 B2 * | 10/2002 | Prince | A61M 5/007 324/309 |
| 6,484,118 B1 | 11/2002 | Govari | |
| 6,493,575 B1 * | 12/2002 | Kesten | A61B 6/12 600/431 |
| 6,535,756 B1 | 3/2003 | Simon et al. | |
| 6,564,085 B2 * | 5/2003 | Meaney | G01R 33/5635 324/309 |
| 6,618,612 B1 | 8/2003 | Acker et al. | |
| 6,675,037 B1 * | 1/2004 | Tsekos | A61B 90/17 600/419 |
| 6,690,963 B2 | 2/2004 | Ben Haim | |
| 6,711,429 B1 * | 3/2004 | Gilboa | A61B 5/06 600/407 |
| 6,711,433 B1 * | 3/2004 | Geiger | G06T 11/008 378/98.12 |
| 6,741,881 B2 * | 5/2004 | Prince | G01R 33/5601 324/309 |
| 6,748,259 B1 * | 6/2004 | Benaron | A61B 5/0084 600/478 |
| 6,783,752 B2 * | 8/2004 | Østensen | A61K 49/223 424/9.52 |
| 6,879,853 B2 * | 4/2005 | Meaney | G01R 33/5601 324/309 |
| 6,889,072 B2 * | 5/2005 | Prince | A61B 5/411 324/309 |
| 7,604,601 B2 * | 10/2009 | Altmann | A61B 6/488 600/463 |
| 7,756,576 B2 | 7/2010 | Levin | |
| 7,848,787 B2 | 12/2010 | Osadchy | |
| 7,869,865 B2 | 1/2011 | Govari et al. | |
| 7,945,309 B2 * | 5/2011 | Govari | A61B 5/06 606/130 |
| 7,974,680 B2 * | 7/2011 | Govari | A61B 5/06 606/130 |
| 10,555,776 B2 * | 2/2020 | Govari | A61B 18/1492 |
| 10,646,197 B2 * | 5/2020 | Govari | A61B 8/12 |
| 2002/0065455 A1 | 5/2002 | Ben Haim et al. | |
| 2002/0068866 A1 * | 6/2002 | Zikorus | A61B 18/1492 600/478 |
| 2003/0047083 A1 * | 3/2003 | Prince | G01R 33/5635 99/325 |
| 2003/0055400 A1 * | 3/2003 | Seward | A61B 17/3478 600/431 |
| 2003/0078485 A1 | 4/2003 | Hartlep | |
| 2003/0120150 A1 | 6/2003 | Govari | |
| 2003/0236458 A1 * | 12/2003 | Hochman | A61B 5/0059 600/431 |
| 2004/0068178 A1 | 4/2004 | Govari | |
| 2004/0092813 A1 * | 5/2004 | Takizawa | G01R 33/563 600/423 |
| 2004/0101088 A1 * | 5/2004 | Sabol | A61B 6/481 378/4 |
| 2004/0141921 A1 * | 7/2004 | Ostensen | A61K 49/223 424/9.52 |
| 2005/0054913 A1 * | 3/2005 | Duerk | G01R 33/287 600/423 |
| 2005/0054914 A1 * | 3/2005 | Duerk | G01R 33/287 600/423 |
| 2005/0118104 A1 * | 6/2005 | Ostensen | A61K 49/223 424/9.52 |
| 2008/0183074 A1 | 7/2008 | Carls et al. | |
| 2013/0303892 A1 | 11/2013 | Zhao et al. | |
| 2017/0065206 A1 | 3/2017 | Bozkaya et al. | |
| 2018/0070855 A1 | 3/2018 | Eichler | |
| 2018/0235709 A1 | 8/2018 | Donhowe et al. | |
| 2018/0286517 A1 * | 10/2018 | Grass | G16H 30/20 |

OTHER PUBLICATIONS

European Search Report for Application No. 20160942.7-1115, dated May 20, 2020.

* cited by examiner

SHOWING CATHETER IN BRAIN

FIELD OF THE INVENTION

The present invention relates to medical devices, and in particular, but not exclusively, to catheter-based cerebrovascular tracking systems.

BACKGROUND

Realtime brain imaging is generally performed using a fluoroscopy technique. For example, in cerebral angiography, a catheter is inserted into an artery in the leg or arm through a small incision in the skin. Using x-ray guidance, the catheter is navigated to the area being examined. Once there, contrast material is injected through the catheter tube and images are captured using ionizing radiation.

US Patent Publication 2003/0078485 of Hartlep describes a device for electrophysiologically localizing target areas in the brain, comprising a multi-channel microprobe which at its active end comprises a multitude of tightly packed microelectrodes arranged axially in rows, via which electrophysiological efferences are obtained in the target area and forwarded to an evaluating unit, wherein the microprobe is assigned to a tracking device which allows the microprobe to be positionally detected by means of a neuronavigation system and the insertion of the probe to be stereotactically planned.

US Patent Publication 2008/0183074 of Carls, et al., describes an integrated surgical navigational and neuromonitoring system. The integrated system provides real-time visualization of an instrument relative to a visualization of patient anatomy. The integrated system also acquires and incorporates neuromonitoring information into the visualization of the patient anatomy. The integrated system is further capable of integrating neurodiagnostic information, such as nerve conduction information, with anatomical and instrument position information to evaluate changes in neural integrity and develop treatment strategies.

U.S. Pat. No. 6,535,756 to Simon, et al., describes an apparatus and methods for use within an image-guided surgical navigation system for the storage and measurement of trajectories for surgical instruments. An icon representing the real-time trajectory of a tracked instrument is overlaid on one or more pre-acquired images of the patient. At the surgeon's command, the navigation system can store multiple trajectories of the instrument and create a static icon representing each saved trajectory for display. The surgeon may also measure a planar angle between any two trajectories. The angle is computed in the plane of the image, and therefore will be computed separately for each image displayed. Furthermore, the surgeon has the option of computing and displaying the three-dimensional distance between two points defined by any two trajectories.

SUMMARY

There is provided in accordance with an embodiment of the present disclosure, a medical tracking system, including a catheter configured to be inserted into, and moved around in, blood vessels of a body-part of a living subject, and including a flexible shaft having a deflectable distal end, and a location tracking transducer in the distal end, the location tracking transducer being configured to output a signal that is indicative of a location of the transducer in the body-part, a tracking subsystem configured to track locations of the distal end of the catheter over time responsively to the signal, a display, and processing circuitry configured to add the tracked locations of the distal end to a movement log, and render to the display an image of at least part of the body-part of the living subject with a representation of a length of the shaft of the catheter in at least one blood vessel of the blood vessels of the body-part, with respective positions along the length of the shaft being located in the image responsively to respective ones of the tracked locations from the movement log.

Further in accordance with an embodiment of the present disclosure the processing circuitry is configured to render the length of the shaft so that the respective positions along the length of the shaft are located in the image responsively to the respective tracked locations a temporal order of the tracked locations in the movement log with one of the positions of the length of the shaft closest to a distal tip of the catheter corresponding with a most recent one of the tracked locations in the movement log.

Still further in accordance with an embodiment of the present disclosure responsively to the distal end of the catheter being retracted in the at least one blood vessel with respect to at least one tracked location of the tracked locations included in the movement log, the processing circuitry is configured to remove the at least one tracked location from the movement log yielding an amended movement log, and render the representation of the length of the shaft the amended movement log.

Additionally, in accordance with an embodiment of the present disclosure the processing circuitry is configured to confirm that the catheter has been retracted in the at least one blood vessel with respect to the at least one tracked location responsively to at least the distal end doubling back on a route defined by at least some of the tracked locations included in the movement log.

Moreover, in accordance with an embodiment of the present disclosure the processing circuitry is configured to define sides of the route based on at least a given radius around a line connecting the at least some tracked locations.

Further in accordance with an embodiment of the present disclosure the processing circuitry is configured to register a scanned image of at least part of the body-part delineating the blood vessels, compute locations of walls of the at least one blood vessel from data of the registered image, and define sides of the route as being bound by walls of the at least one blood vessel.

Still further in accordance with an embodiment of the present disclosure the catheter has a diameter of 1 mm or less.

Additionally, in accordance with an embodiment of the present disclosure the tracking subsystem includes a location pad having at least one magnetic field radiator configured to transmit alternating magnetic fields into a region where the body-part is located, the location tracking transducer including a coil to detect at least part of the transmitted alternating magnetic fields.

There is also provided in accordance with another embodiment of the present disclosure, a medical tracking method, including tracking locations of a deflectable distal end of a flexible shaft of a catheter configured to be inserted into, and moved around in, blood vessels of a body-part of a living subject over time responsively to a signal output by a location tracking transducer, the signal being indicative of a location of the location tracking transducer in the body-part, adding the tracked locations of the distal end to a movement log, and rendering to a display an image of at least part of the body-part of the living subject with a representation of a length of the shaft of the catheter in at least one blood vessel of the body-part, with respective positions along the length of the shaft being located in the image responsively to respective ones of the tracked locations from the movement log.

Moreover in accordance with an embodiment of the present disclosure the rendering includes rendering the length of the shaft so that the respective positions along the length of the shaft are located in the image responsively to the respective tracked locations a temporal order of the tracked locations in the movement log with one of the positions of the length of the shaft closest to a distal tip of the catheter corresponding with a most recent one of the tracked locations in the movement log.

Further in accordance with an embodiment of the present disclosure, the method includes, responsively to the distal end of the catheter being retracted in the at least one blood vessel with respect to at least one tracked location of the tracked locations included in the movement log, removing the at least one tracked location from the movement log yielding an amended movement log, wherein the rendering includes rendering the representation of the length of the shaft the amended movement log.

Still further in accordance with an embodiment of the present disclosure, the method includes confirming that the catheter has been retracted in the at least one blood vessel with respect to the at least one tracked location responsively to at least the distal end doubling back on a route defined by at least some of the tracked locations included in the movement log.

Additionally, in accordance with an embodiment of the present disclosure, the method includes defining sides of the route based on at least a given radius around a line connecting the at least some tracked locations.

Moreover, in accordance with an embodiment of the present disclosure, the method includes registering a scanned image of at least part of the body-part delineating the blood vessels, computing locations of walls of the at least one blood vessel from data of the registered image, and defining sides of the route as being bound by walls of the at least one blood vessel.

Further in accordance with an embodiment of the present disclosure the catheter has a diameter of 1mm or less.

Still further in accordance with an embodiment of the present disclosure, the method includes transmitting alternating magnetic fields into a region where the body-part is located, and detecting at least part of the transmitted alternating magnetic fields by a coil location tracking transducer included in the catheter.

There is also provided in accordance with another embodiment of the present disclosure, a software product, including a non-transient computer-readable medium in which program instructions are stored, which instructions, when read by a central processing unit (CPU), cause the CPU to track locations of a deflectable distal end of a flexible shaft of a catheter configured to be inserted into, and moved around in, blood vessels of a body-part of a living subject over time responsively to a signal output by a location tracking transducer, the signal being indicative of a location of the location tracking transducer in the body-part, add the tracked locations of the distal end to a movement log, and render to a display an image of at least part of the body-part of the living subject with a representation of a length of the shaft of the catheter in at least one blood vessel of the body-part, with respective positions along the length of the shaft being located in the image responsively to respective ones of the tracked locations from the movement log.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

Figure 1A:
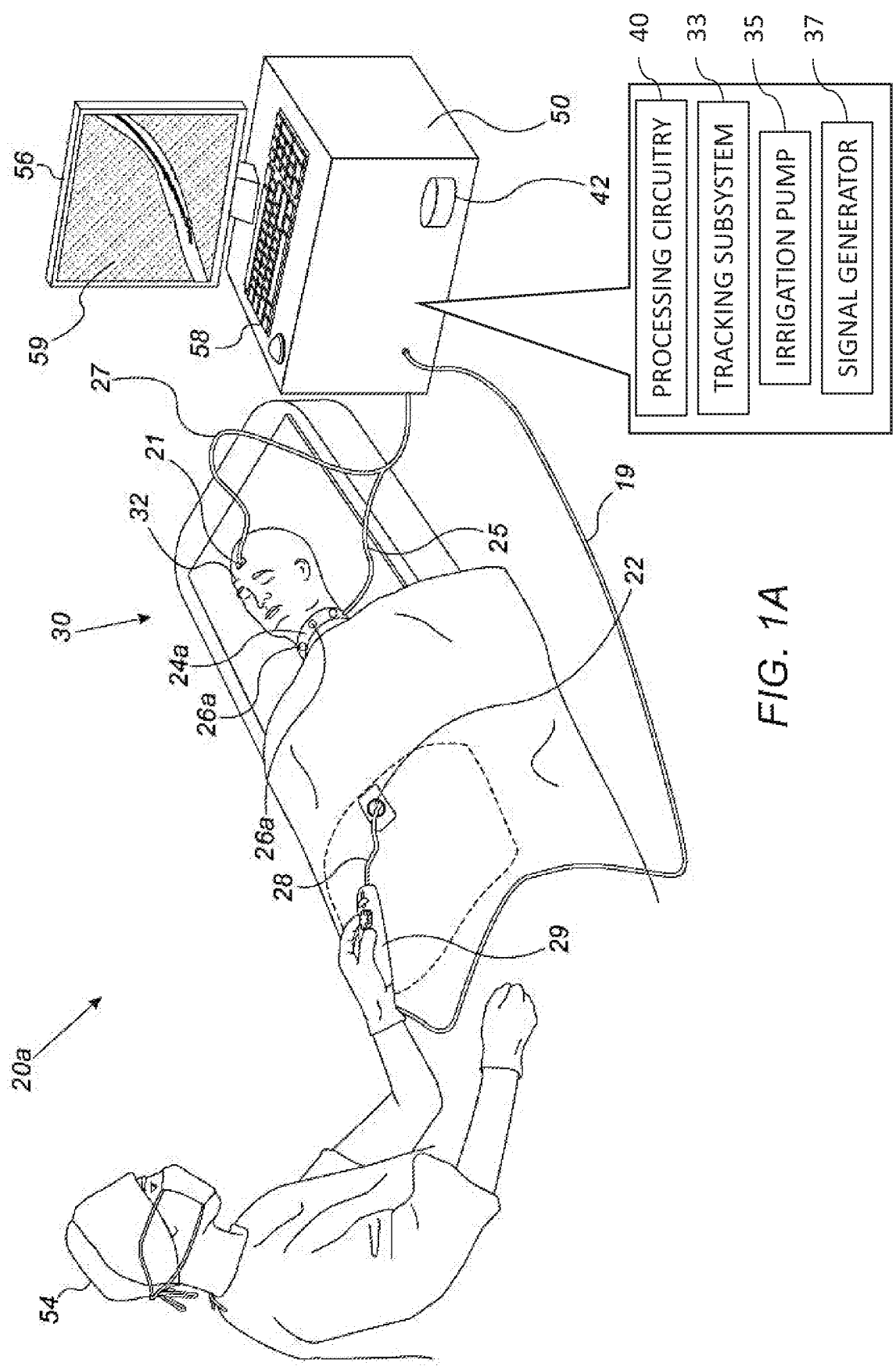
FIGS. 1A and 1B are schematic, pictorial illustrations of catheter-based cerebrovascular tracking systems, in accordance with embodiments of the present invention.

Blood vessels in the brain may be interconnected via a variety of routes and therefore a catheter inserted into the brain may travel between two points using a variety of different routes. Partly due to the complexity of the blood vessel routes as well as the narrow width of the blood vessels, it can be very challenging to navigate a catheter in the brain. It is very important for a physician to see the positioning of the whole catheter in the brain, and not just its distal tip, in order to enable efficient navigation of the catheter in the brain, as time is generally of the essence with brain procedures, e.g., to diagnose and treat a stroke victim.

If a physician takes a wrong route with the catheter, the physician generally wants to take minimal steps to find the correct route in the complex maze of brain blood vessels. Allowing the physician to see the positioning of the whole catheter in the brain will aid the physician to efficiently find the best and quickest route to the desired location.

Although the catheter may be seen under fluoroscopy, due to radiation exposure, it is preferable not to use fluoroscopy.

One solution is to use multiple tracking sensors along the length of the catheter to determine the location of the different points on the catheter. However, due to the size of the blood vessels in the brain, the catheter may be about 1 mm in diameter, thereby limiting the number of wires that can be included in the catheter for operating the multiple sensors.

Using a single tracking sensor installed close to the distal tip of the catheter gives the location of the distal tip.

However, the remainder of the catheter cannot be deduced from the current tracked location of the distal tip as the catheter may have travelled down a variety routes to arrive at the current location of the distal tip.

Embodiments of the present invention, provide a system that finds the positioning of a length of a shaft of a catheter in a brain of a living subject based on a movement log (e.g., history log) of the tracked locations of a point (e.g., the distal tip) of the catheter. The tracked locations are generally derived from readings received from a single tracking transducer (e.g., a single axis sensor) disposed in the distal end of the catheter.

An image of at least part of the brain of the living subject, based on a pre-registered image, is rendered to a display with a representation of the length of the shaft of the brain catheter in at least one blood vessel of the brain with respective positions along the length of the shaft being located in the image responsively to respective tracked locations from the movement log.

As the catheter is advanced in the blood vessels, the tracked locations are added to the movement log, and the representation of the length of the shaft of the brain catheter is updated to reflect the new tracked locations which have been added to the movement log.

In some embodiments, the movement log is adjusted when the catheter is partly retracted so that tracked locations corresponding to the retracted portion of the movement log are removed from the movement log. If the movement log is not adjusted based on the partial retraction of the catheter, using the movement log to render the representation of the length of the shaft of the brain catheter will make it appear to the physician as though the catheter performed a U-turn in the blood vessel when in fact the catheter was retracted.

When the catheter is partially retracted, although the tracked locations computed during the retraction may be close to the tracked locations of the same route (e.g., the same blood vessel(s)) in which the catheter was advanced, the tracked locations during retraction are very unlikely to be exactly the same as during the advancement of the catheter. Therefore, in order to identify whether the catheter has been partly retracted or simply advanced along another route close to the current route, the sides of the current route (e.g., the walls of the blood vessels) along which the catheter has travelled so far need to be computed or estimated.

The sides of the current route may be estimated based on defining a circle of a given radius around a line connecting the tracked locations in the movement log thereby creating an elongated tube representing the route. However, as the blood vessels may be various widths, and in some cases narrow blood vessels may be very close together, the above estimation may not be accurate enough for certain applications.

In some embodiments, the sides of the route may be defined by locations of the walls of the blood vessels through which the catheter has travelled. In some embodiments, a scanned image (e.g., an Angiogram CT) of at least part of the brain delineating the blood vessels may be registered with the system and the locations of the walls of the blood vessels may be computed from data of the registered image.

The embodiments described herein have been described with reference to the brain. However, the invention may be implemented to track a catheter in blood vessels of any suitable body-part.

System Description

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Figure 1B:
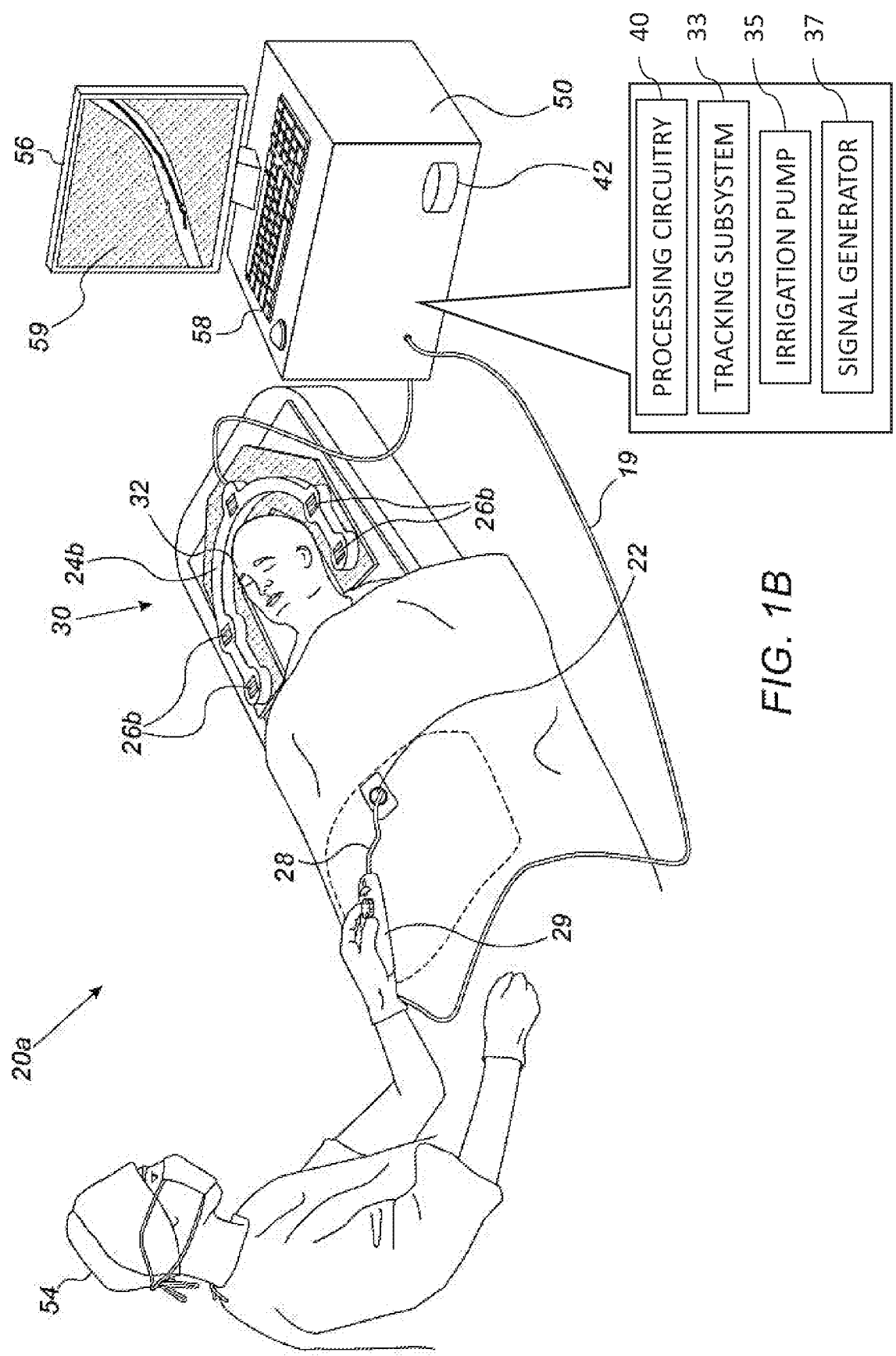

FIGS. 1A and 1B are schematic, pictorial illustrations of catheter-based cerebrovascular tracking systems 20a and 20b, in accordance with embodiments of the present invention.

In some embodiments, prior to performing the catherization procedure, CT images of a patient 32 are acquired. The CT images are stored in a memory 42 for subsequent retrieval by processing circuitry 40. The processing circuitry 40 uses the images to present, for example, a brain section image 59 on a display 56. In another embodiment, during the disclosed catheterization, systems 20a and 20b register a position of a distal end of a brain catheter 28 inside the patient's brain, with frames of reference of brain images of the patient 32. The position of the distal end of the brain catheter 28 may be tracked using a tracking subsystem 33, which tracks position and orientation coordinates of a location tracking transducer fitted at the distal end. The location tracking transducer is configured to output a signal that is indicative of a location of the transducer in the body-part (e.g. the brain). This signal is processed by the tracking subsystem 33 to track the locations of the distal end of the brain catheter 28 over time. In some embodiments, the tracking subsystem 33 may be a magnetic tracking subsystem described in more detail below and the location tracking transducer includes at least one coil, described in more detail with reference to FIG. 3. In other embodiments, the tracking subsystem 33 may be an electrically-based tracking subsystem using multiple head surface electrodes (not shown) to track the position of the brain catheter 28 based on a signal emitted by at least one electrode (comprised in the location tracking transducer) of the brain catheter 28. The tracking subsystem 33 may be implemented using any suitable location tracking subsystem, for example, but not limited to, an ultrasound-based tracking system where the location tracking transducer includes at least one ultrasound transducer. Using tracking subsystem 33, a physician 54 advances the distal end of the brain catheter 28 through blood vessels, described in more detail with reference to FIGS. 3-12.

In system 20a, shown in FIG. 1A, a location pad 24a is implemented as a collar around the neck of patient 32. By putting location pad 24a around the neck, location pad 24a is configured to automatically compensate for patient head movement. Location pad 24a comprises magnetic field radiators 26a which are fixed in position relative to the head of patient 32 and which transmit alternating sinusoidal magnetic fields into a region 30 where the head of patient 32 is located. A console 50 electrically drives radiators 26a via a cable 25. In an embodiment, further compensation of head motion is provided by attaching a reference sensor 21 to the patient's forehead. Console 50 is configured to receive signals from reference sensor 21 via a cable 27. A location tracking system that comprises a neck collar location pad is described in U.S. patent application Ser. No. 16/248,393, filed Jan. 15, 2019, entitled "Position Sensor on Brain Clot Sheath and Location Pad Collar," which is assigned to the assignee of the present patent application and whose disclosure is incorporated herein by reference.

Physician 54, operating system 20a, holds a brain catheter controller handle 29, which is connected to the proximal end of brain catheter 28. Controller handle 29 allows the physician 54 to advance and navigate brain catheter 28 in the brain, for example, through an entry point 22 at an artery at a thigh of patient 32. As noted above and described below, physician 54 navigates the distal end of brain catheter 28 with the aid of real-time images rendered based on position and orientation signals from the location tracking transducer fitted at the distal end of brain catheter 28. Console 50 receives the position signals via a cable 19 that connects to brain catheter 28 via handle 29.

Elements of system 20a, including radiators 26a, are controlled by processing circuitry 40, comprising a processing unit communicating with one or more memories (e.g., the memory 42). Processing circuitry 40 may be mounted in console 50, which comprises operating controls 58 that typically include a keypad and/or a pointing device such as a mouse or trackball. Physician 54 uses operating controls on handle 29 to interact with the processing circuitry 40 while performing the registration of system 20a. During the registration process, an image 59 of a brain section is presented on display 56. Subsequent to the registration process described above, physician 54 uses the operating controls to advance the distal end of brain catheter 28 to one or more desired locations in the brain.

Processing circuitry 40 uses software stored in the memory 42 to operate system 20a. In practice, some or all of the functions of the processing circuitry 40 may be combined in a single physical component or, alternatively, implemented using multiple physical components. These physical components may comprise hard-wired or programmable devices, or a combination of the two. In some embodiments, at least some of the functions of the processing circuitry 40 may be carried out by a programmable processor under the control of suitable software. This software may be downloaded to a device in electronic form, over a network, for example. Alternatively, or additionally, the software may be stored in tangible, non-transitory computer-readable storage media, such as optical, magnetic, or electronic memory.

In some embodiments, the console 50 may also include an irrigation pump 35 for pumping irrigation fluid through the brain catheter 28 described in more detail with reference to FIGS. 2A and 2B. In some embodiments, the console 50 may include a signal generator 37 also described in more detail with reference to FIGS. 2A and 2B.

System 20b, shown in FIG. 1B, has a different magnetic location pad design, namely a location pad 24b. As seen, location pad 24b is fixed to the bed, and irradiators 26b surround a patient headrest horizontally. In this example, system 20b lacks reference sensor 21, and therefore the head of the patient must be harnessed to prevent motion of the head. In some embodiments the reference sensor 21 may be included. Other components of system 20b are generally identical to those of system 20a. A location tracking system using a location pad similar to location pad 24b is described in U.S. patent application Ser. No. 15/674,380, filed Aug. 10, 2017, entitled "ENT Image Registration," which is assigned to the assignee of the present patent application and whose disclosure is incorporated herein by reference.

Systems 20a and 20b shown in FIGS. 1A and 1B are chosen purely for the sake of conceptual clarity. Other system elements may be included, for example additional controls on handle 29 for controlling additional tooling such as for drug delivery.

CARTO® magnetic tracking systems, which track a location and orientation of a magnetic position sensor in an organ of a body using techniques similar to those applied by systems 20a and 20b, are produced by Biosense-Webster (Irvine, Calif.). In general, position sensing using current distribution measurements and/or external magnetic fields are described in detail in U.S. Pat. Nos. 5,391,199, 6,690, 963, 6,484,118, 6,239,724, 6,618,612, 6,332,089, 7,756,576, 7,869,865, and 7,848,787, in PCT Patent Publication WO 96/05768, and in U.S. Patent Application Publications 2002/0065455 A1, 2003/0120150 A1 and 2004/0068178 A1, whose disclosures are all incorporated herein by reference.

Figure 2A:
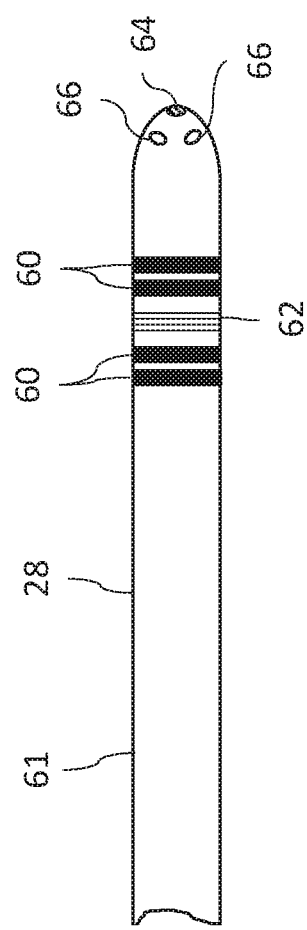
FIGS. 2A and 2B are side and end views, respectively, of brain catheter for use with the systems of FIGS. 1A and 1B.
Figure 2B:
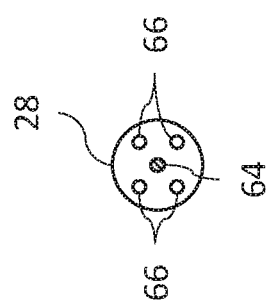

Reference is now made to FIGS. 2A and 2B, which are side and end views, respectively, of the brain catheter 28 for use with the systems 20a and 20b of FIGS. 1A and 1B.

The brain catheter 28 is configured to be inserted into, and moved around in, blood vessels of a brain of a living subject. The brain catheter 28 includes a flexible shaft 61 having a distal end, which is generally deflectable (flexible) and is dimensioned to fit into blood vessels of the brain. The brain catheter 28 is generally formed as an elongated cylinder with a tapered distal tip providing a smooth surface without any sharp corners or edges. In some embodiments, the brain catheter 28 has a diameter of 1 mm or less. In some embodiments, the brain catheter 28 is magnetic resonance imaging (MRI) compatible. An outer casing of the brain catheter 28 may be composed of polyamide or any suitable material.

The brain catheter 28 may include at least one bipolar electrode pair 60. FIG. 2A shows the brain catheter 28 having two bipolar electrode pairs 60. The brain catheter 28 may have any suitable number of bipolar electrode pairs 60. Each bipolar electrode pair 60 may detect signals indicative of electrical activity in the brain without having to use body/head surface electrodes for detecting the electrical activity. In some embodiments, body/head surface electrodes may be used as part of the tracking subsystem 33 to track a location of the bipolar electrode pair(s) 60 of the brain catheter 28. In some embodiments, the brain catheter 28 may include any suitable number of unipolar and/or bipolar electrodes for mapping and/or ablation purposes. In other embodiments, the brain catheter 28 may not include any electrodes. The bipolar electrode pair 60 may be composed of any suitable material for example, but not limited to, platinum-iridium alloy. The electrodes may have any suitable width, for example, 0.2 mm to 0.6 mm, and typically 0.4 mm.

In FIG. 2A, the location tracking transducer 62 is disposed between the two sets of bipolar electrode pairs 60. The location tracking transducer 62 may be disposed in any suitable location in the distal end, e.g., near the distal tip of the brain catheter 28. The location tracking transducer 62 is configured to output a signal that is indicative of a location of the transducer 62 in the body-part (e.g., the brain). The tracking subsystem 33 is configured to track the locations of a point of the distal end of the brain catheter 28 over time responsively to the signal output by the location tracking transducer 62. As described above with reference to FIGS. 1A and 1B, the tracking subsystem 33 includes the location pad 24 having the magnetic field radiator(s) 26 configured to transmit alternating magnetic fields into the region 30 where the brain is located. In some embodiments, the location tracking transducer 62 includes a coil to detect at least part of the transmitted alternating magnetic fields. FIG. 2A shows the coil as being wound close to the surface of the brain catheter 28. In some embodiments, the coil is disposed beneath an outer casing of the brain catheter 28 and is generally disposed coaxially with the brain catheter 28. The coil may have any suitable diameter, for example, between 0.5 mm and 1 mm, and in some embodiments, 0.65 mm.

The brain catheter 28 may include an optical fiber and lens 64 disposed therein to capture images of the brain. In other embodiments, the optical fiber and lens 64 is optional. The brain catheter 28 includes at least one irrigation channel 66 therein. The irrigation pump 35 (FIG. 1) is configured to pump irrigation fluid via the irrigation channel(s) 66 into the brain to provide cooling when ablation is used. The irrigation fluid may be any suitable fluid, for example, but not limited to, a saline. The irrigation rate may be any suitable irrigation rate, for example, but not limited to, in the range of 5 to 25 ml/min., and typically 15 ml/min. The irrigation fluid may also provide lubrication for moving the brain catheter 28 as well as preventing blood clots. In other embodiments, the irrigation channel(s) 66 and the irrigation pump 35 are optional.

One or more of the bipolar electrodes 60 (or other electrodes) may be used to provide ablation functionality. The signal generator 37 may be configured to generate a suitable signal to be applied by the electrodes 60 during ablation.

Figure 3:
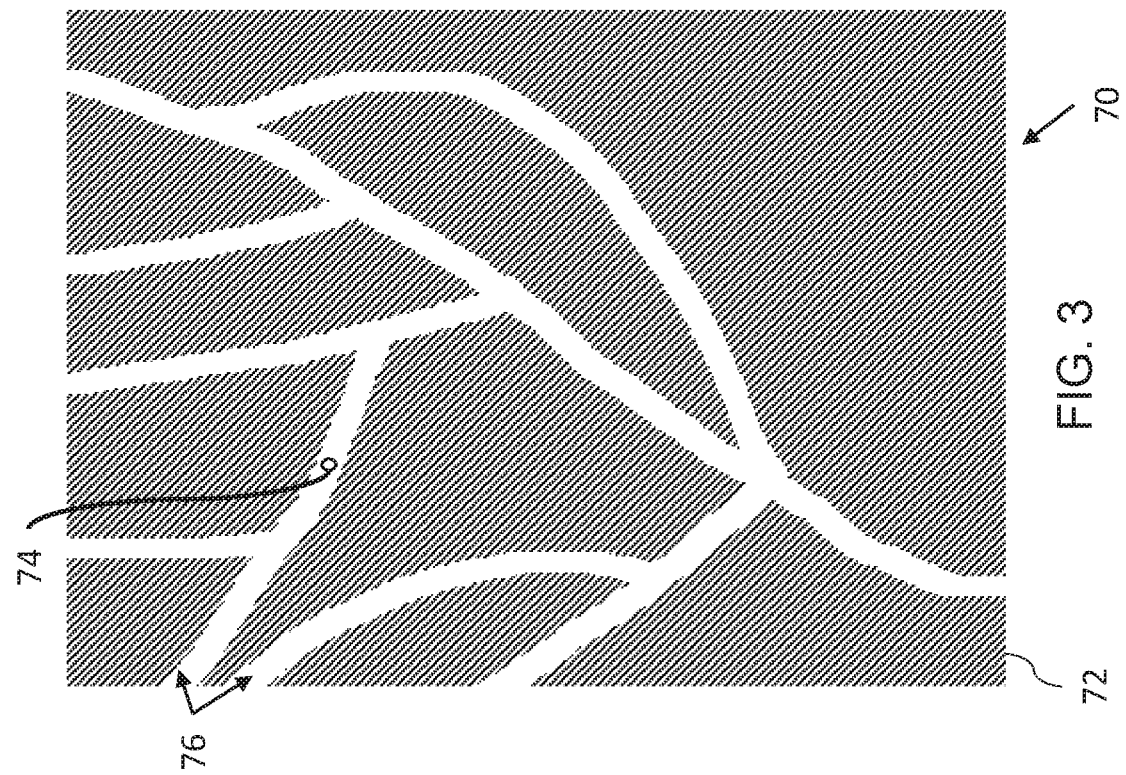
FIG. 3 is a view of an image showing part of a brain and a tracked location of the brain catheter of FIGS. 2A and 2B.

Reference is now made to FIG. 3, which is a view of an image 70 showing part of a brain 72 and a tracked location 74 of the distal tip of the brain catheter 28 of FIGS. 2A and 2B. FIG. 3 indicates that the distal tip of the brain catheter 28 is located in one of a plurality of blood vessels 76 (only some labeled for the sake of simplicity) of the brain 72. It is clearly seen that simply based on the tracked location 74, the rest of the brain catheter 28 could be positioned down any one of the various blood vessels 76.

Figure 4:
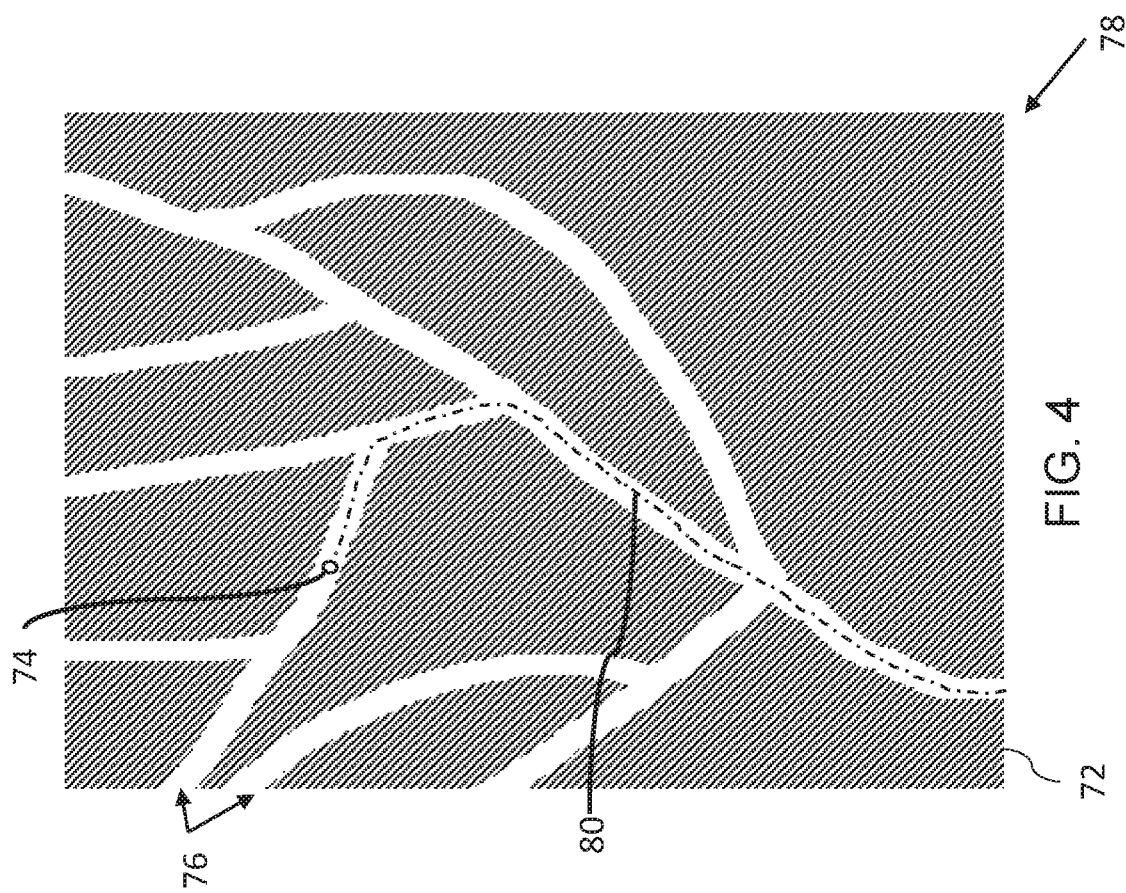
FIG. 4 is view of an image showing a history of the tracked locations of the brain catheter of FIGS. 2A and 2B.

Reference is now made to FIG. 4, which is view of an image 78 showing a history 80 of the tracked locations of the brain catheter 28 of FIGS. 2A and 2B. The history 80 shows where the distal tip of the brain catheter 28 was located over time prior to the current tracked location 74.

Figure 5:
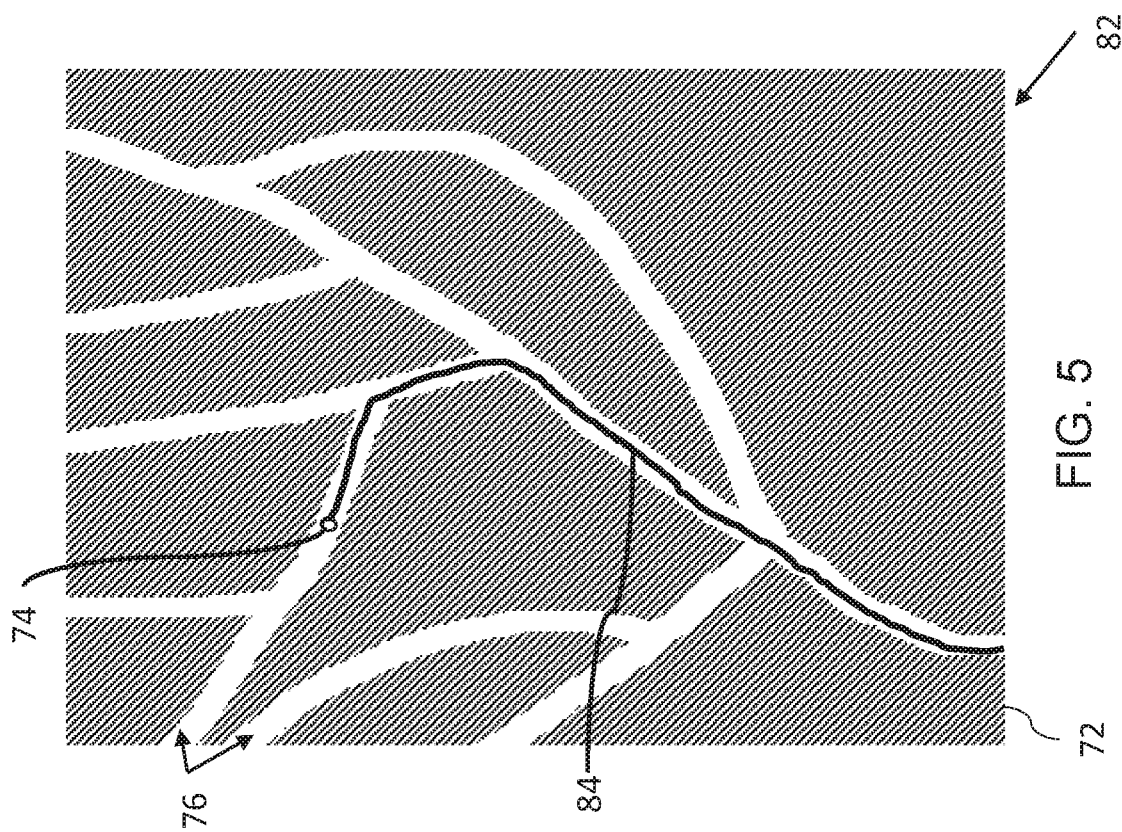
FIG. 5 is a view of an image showing part of the brain with a representation of the brain catheter of FIGS. 2A and 2B.

Reference is now made to FIG. 5, which is a view of an image 82 showing part of the brain 72 with a representation 84 of the brain catheter 28 of FIGS. 2A and 2B. The positioning of the representation 84 of the brain catheter 28 corresponds with the history 80 of FIG. 4. The representation 84 provides an estimate of the current positioning of the brain catheter 28. Due to sideways movement of the brain catheter 28 in the blood vessels 76 over time, the exact positioning of the brain catheter 28 is likely to be slightly different than shown by the representation 84.

Figure 6:
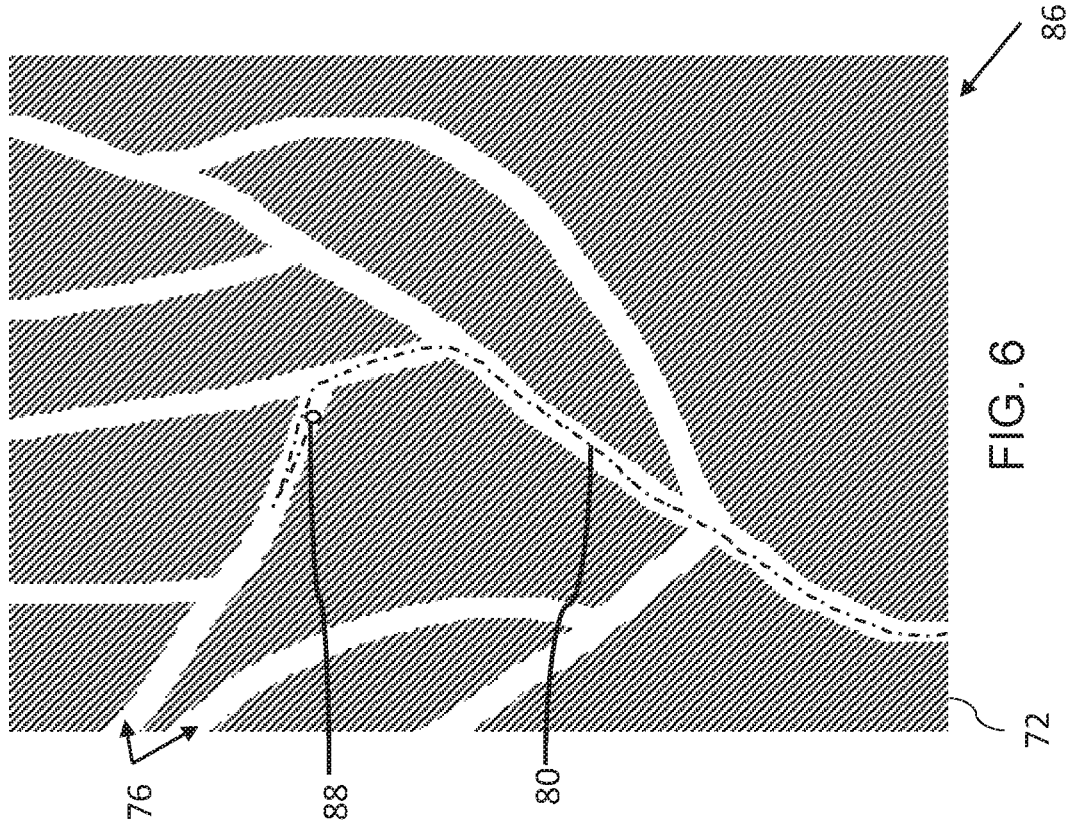
FIG. 6 is a view of an image showing a history of the tracked locations of the brain catheter of FIGS. 2A and 2B after the brain catheter has been partially retracted.

Reference is now made to FIG. 6, which is a view of an image 86 showing the updated history 80 of the tracked locations of the brain catheter 28 of FIGS. 2A and 2B after the brain catheter 28 has been partially retracted in the blood vessel 76 to a new tracked location 88. FIG. 6 shows that the distal tip of the brain catheter 28 had been retracted from the tracked location 74 (FIG. 5) to the new tracked location 88.

Figure 7:
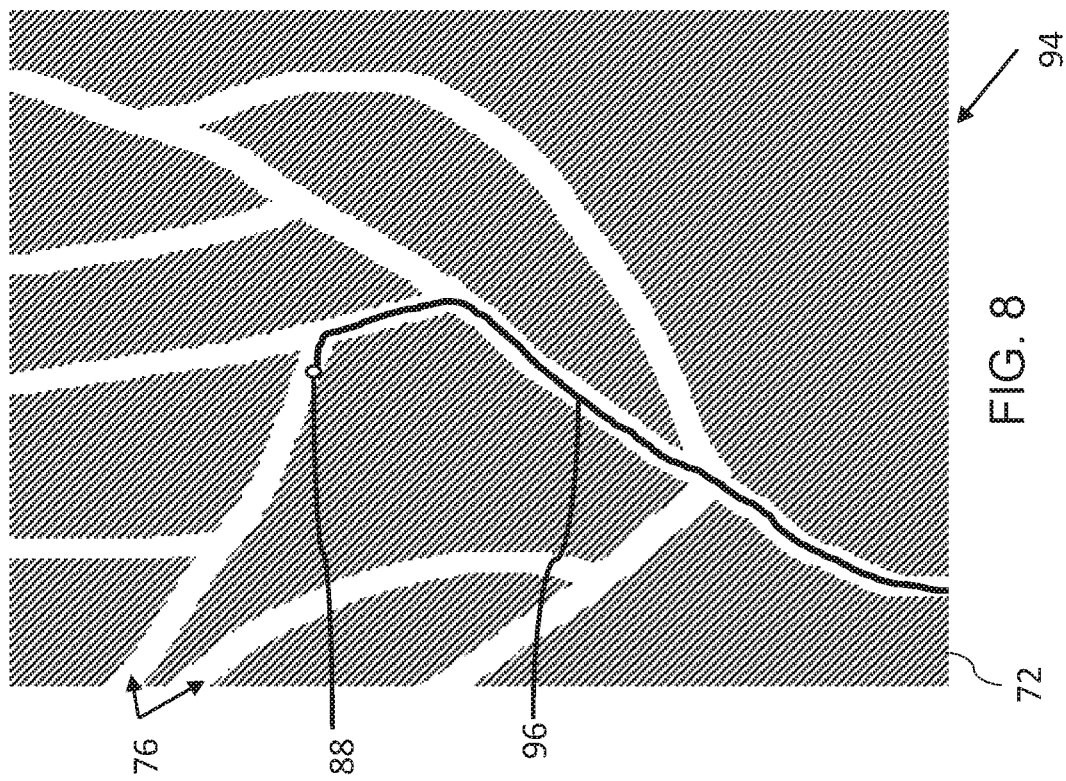
FIG. 7 is a view of an image showing part of the brain with a positioning of a representation of the brain catheter based on the history of FIG. 6.

Reference is now made to FIG. 7, which is a view of an image 90 showing part of the brain 72 with a positioning of a representation 92 of the brain catheter 28 based on the updated history 80 of FIG. 6. If the positioning of the representation 92 of the brain catheter 28 is based on the full updated history 80 it appears that the brain catheter 28 has performed a U-turn in one of the blood vessels 76 as opposed to being retracted in one of the blood vessels 76.

Figure 8:
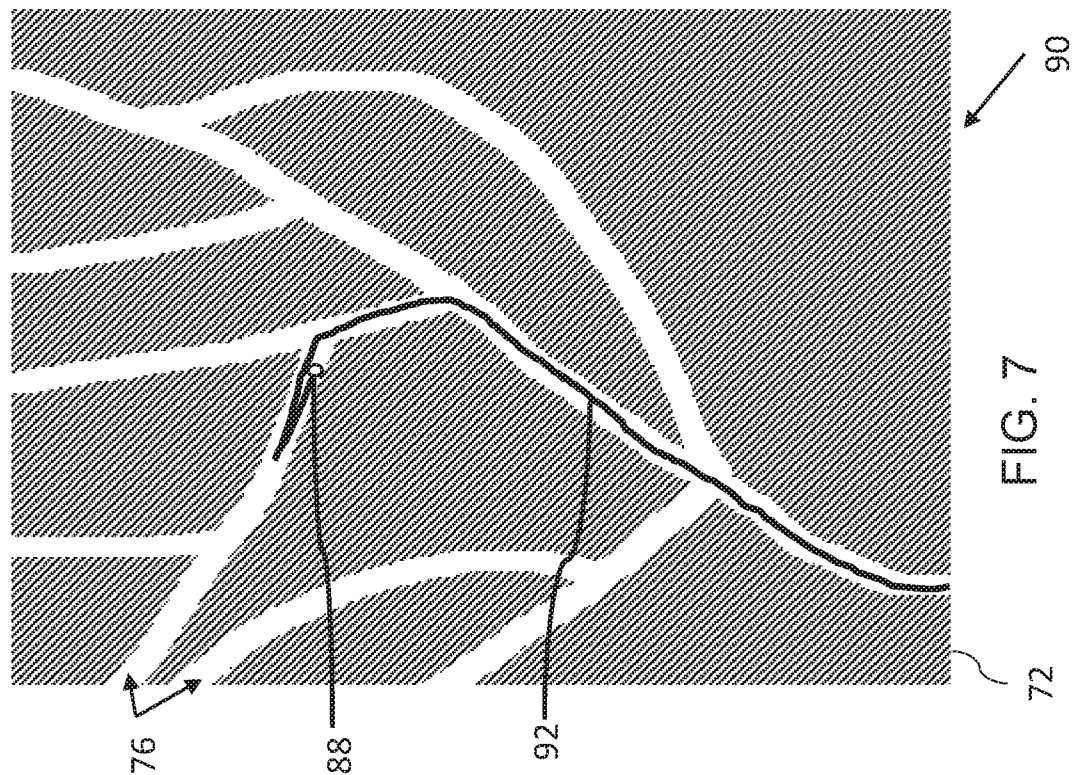
FIG. 8 is a view of an image showing part of the brain with a positioning of a representation of the brain catheter based on correcting the history of FIG. 6 for the partial retraction of the brain catheter.

Reference is now made to FIG. 8, which is a view of an image 94 showing part of the brain 72 with a positioning of a representation 96 of the brain catheter 28 based on correcting the history 80 of FIG. 6 for the partial retraction of the brain catheter 28. In order to correctly show the representation 96, when a recently tracked location (e.g., the new tracked location 88) or locations appear to double-back on a route described by the history 80, the double-backed section of the route described by the history 80 is removed from the history. The representation 96 is then rendered according to the corrected history without the double-backed section.

Figure 9:
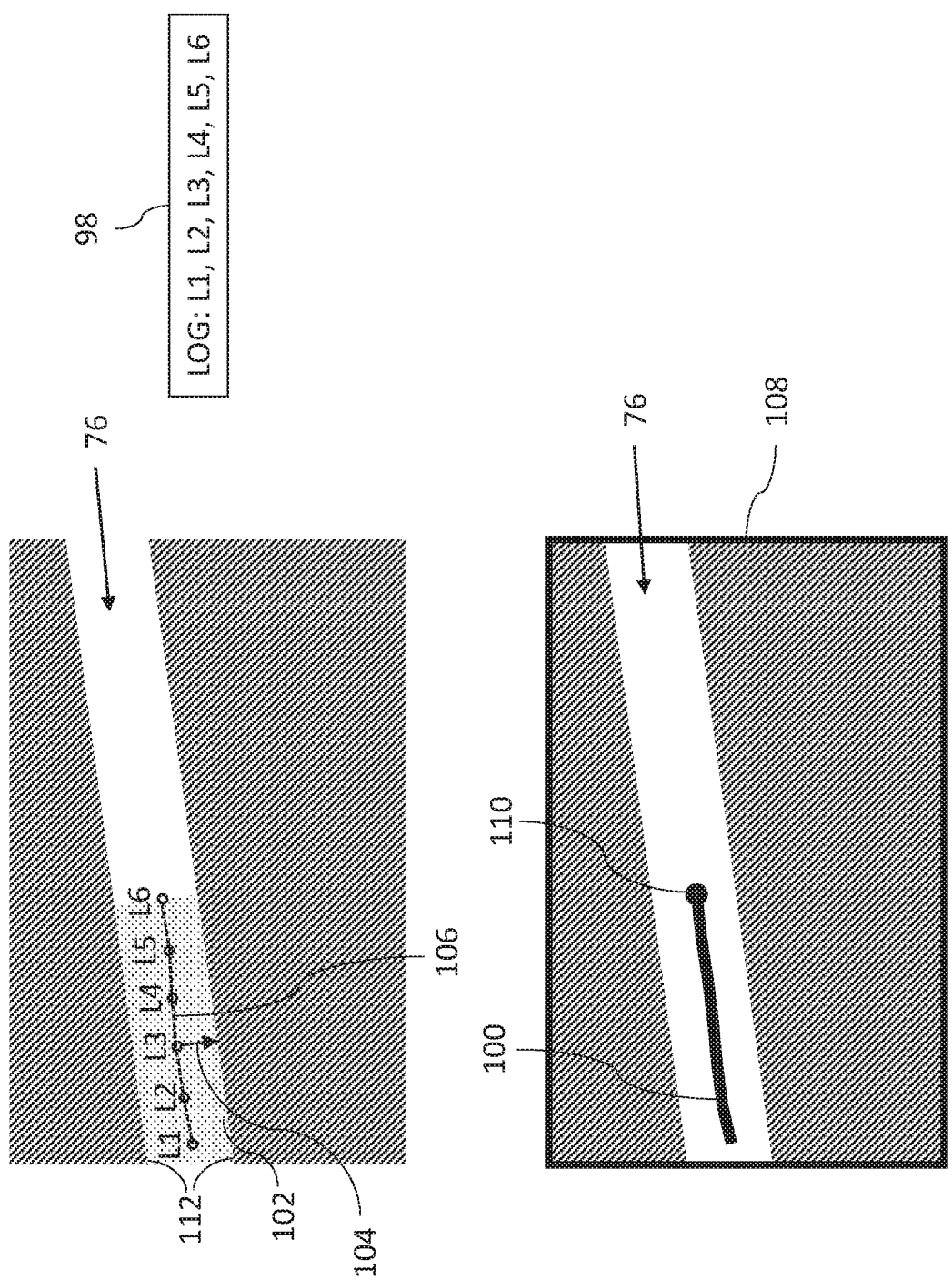
FIGS. 9-11 are views illustrating tracking movement of the brain catheter, updating of a movement log, and rendering the representation of the brain catheter, while the brain catheter is advanced and retracted in the blood vessels for use in the systems of FIGS. 1A and 1B.
Figure 10:
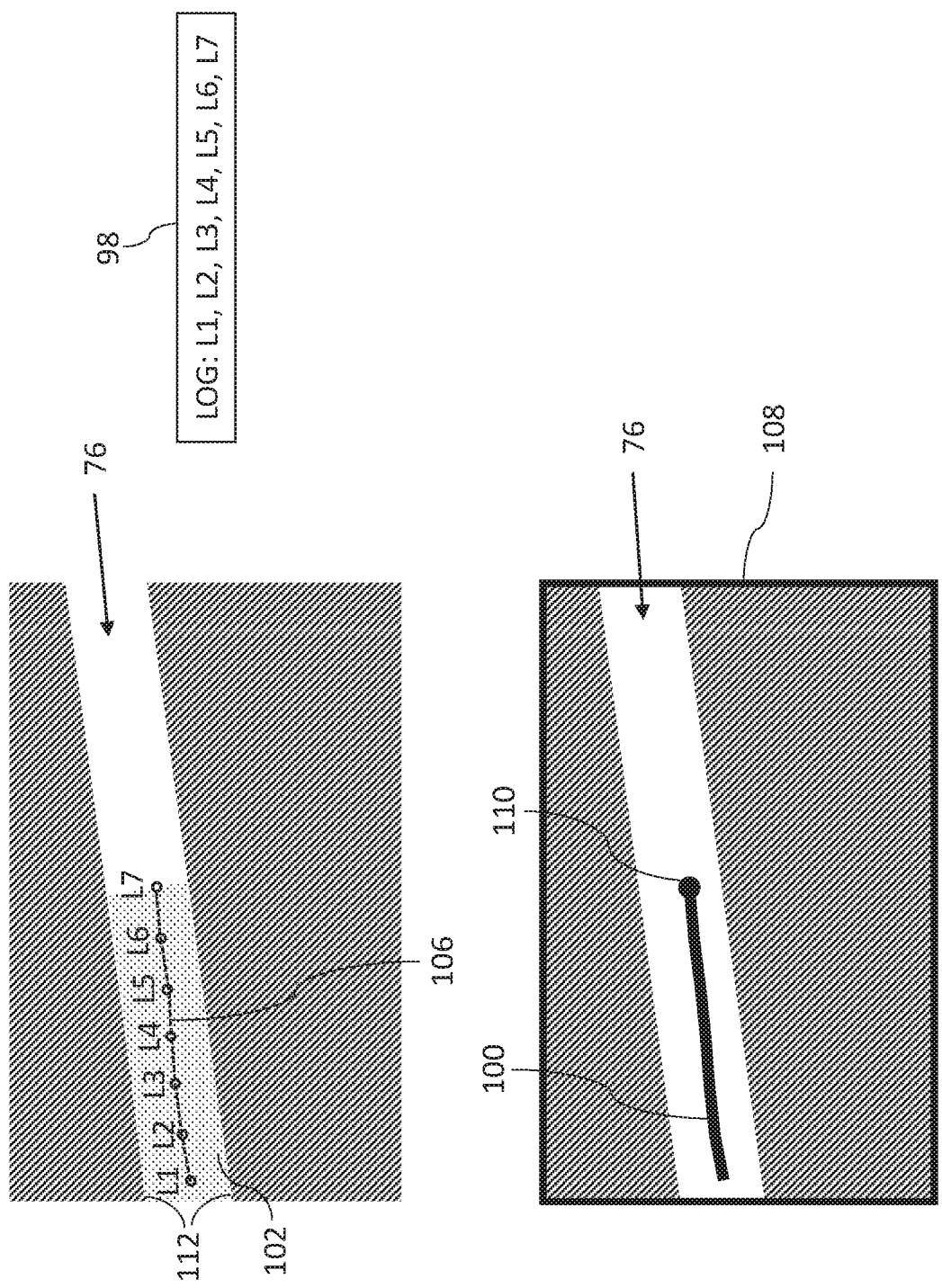
Figure 11:
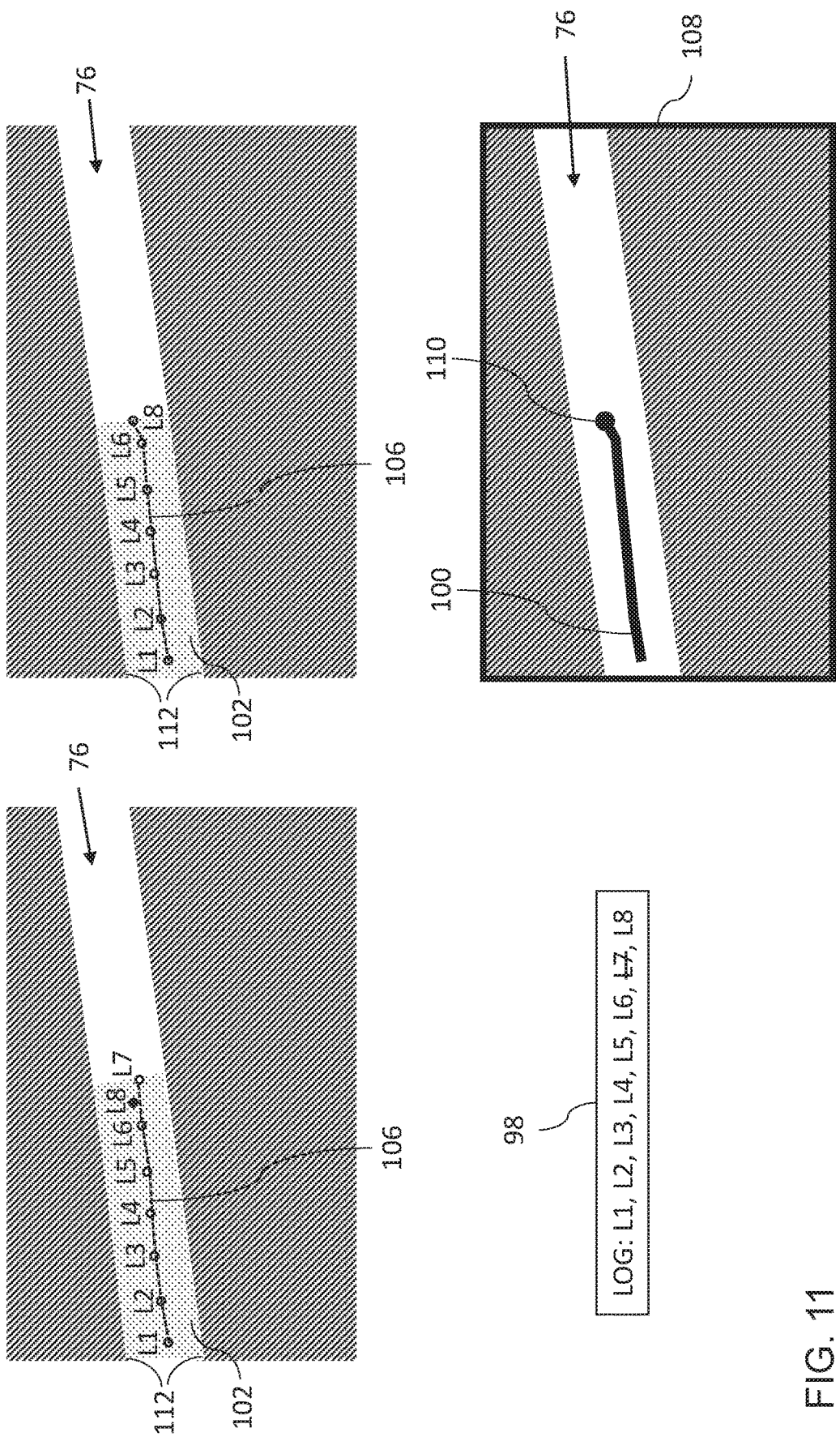

Reference is now made to FIGS. 9-11, which are views illustrating tracking movement of the brain catheter 28 of FIGS. 2A and 2B, updating of a movement log 98, and rendering a representation 100 of the brain catheter 28, while the brain catheter is advanced and retracted in the blood vessels 76 for use in the systems 20a and 20b of FIGS. 1A and 1B.

FIG. 9 shows that the distal end of the brain catheter 28 has been advanced in one of the blood vessels 76 and moved from location L1 to location L6, via locations L2, L3, L4 and L5, over time. The movement log 98 mirrors this movement and includes log entries for L1, L2, L3, L4, L5, and L6.

FIG. 9 also shows a route 102 (shown with lighter shading than the surrounding brain tissue) defined by the tracked locations in the movement log 98. Sides 112 of the route 102 may be defined by the walls of the blood vessels 76. Alternatively, the sides of the route 102 may be assumed to be located at a fixed radius around a line 106 connecting the tracked locations (L1, L2, L3, L4, L5, and L6). By way of example, an arrow 104 indicates the fixed radius at the location L3.

FIG. 9 also shows an image 108 including a part of the brain 72, one of the blood vessels 76, and the representation 100 of the brain catheter 28 in the blood vessel 76. The positioning of the representation 100 of the brain catheter 28 corresponds with the tracked locations L1, L2, L3, L4, L5, and L6. A positioning of a representation 110 of the distal tip of the brain catheter 28 corresponds with the latest tracked location L6.

FIG. 10 shows that the distal end of the brain catheter 28 has been further advanced in one of the blood vessels 76 and moved from location L6 to location L7 along the route 102. The movement log 98 mirrors this movement and the tracked location L7 has been added to the movement log 98. FIG. 9 also shows that the route 102 (shown with lighter shading), defined by the tracked locations in the movement log 98, has been expanded to include the tracked location L7. Sides 112 of the route 102 may be defined by the walls of the blood vessels 76. Alternatively, the sides of the route 102 may be assumed to be located at a fixed radius around the line 106 connecting the tracked locations (L1, L2, L3, L4, L5, L6, and L7) as previously discussed with reference to FIG. 9.

FIG. 10 also shows the image 108 including a part of the brain 72, one of the blood vessels 76, and the representation 100 of the brain catheter 28 in the blood vessel 76. The positioning of the representation 100 of the brain catheter 28 now corresponds with the tracked locations L1, L2, L3, L4, L5, L6, and L7. A positioning of the representation 110 of the distal tip of the brain catheter 28 corresponds with the latest tracked location L7.

Now turning to FIG. 11, the top-left quadrant of FIG. 11 shows that a new tracked location L8 has been tracked and received for further processing by the processing circuitry 40 (FIG. 1). It can be seen that L8 has doubled-back over the route 102 and therefore represents a retraction of the brain catheter 28 in the blood vessel 76. Although, L8 is not exactly on the line 106, the route 102 is defined by the sides 112 and therefore, doubly-back on the route 102 is also defined whether the location L8 is within the boundaries of the route 102.

The tracked location(s), included in the movement log 98, that represent the section of the route 102 on which the distal tip was doubled-back, namely L7 in this example, is removed from the movement log 98. To this end, the movement log 98 in FIG. 11 (bottom-left quadrant) shows that L7 has been removed from, and L8 has been added to, the movement log 98. Therefore, the movement log 98 now includes, L1 to L6, and L8.

The top-right quadrant of FIG. 11, illustrates the updated route 102 and updated line 106 defined by the tracked locations of the updated movement log 98.

The bottom-right quadrant of FIG. 11 shows the image 108 including a part of the brain 72, one of the blood vessels 76, and the representation 100 of the brain catheter 28 in the blood vessel 76 positioned according to the tracked retraction of the brain catheter 28. The positioning of the representation 100 of the brain catheter 28 now corresponds with the tracked locations L1, L2, L3, L4, L5, L6, and L8. A positioning of the representation 110 of the distal tip of the brain catheter 28 corresponds with the latest tracked location L8.

By way of further illustration, if the brain catheter 28 is retracted further to a tracked location L9 (not shown) which is behind both L6 and L8 in the route 102, the tracked locations L6 and L8 are removed from the movement log 98 and the tracked location L9 is added to the movement log 98.

Figure 12:
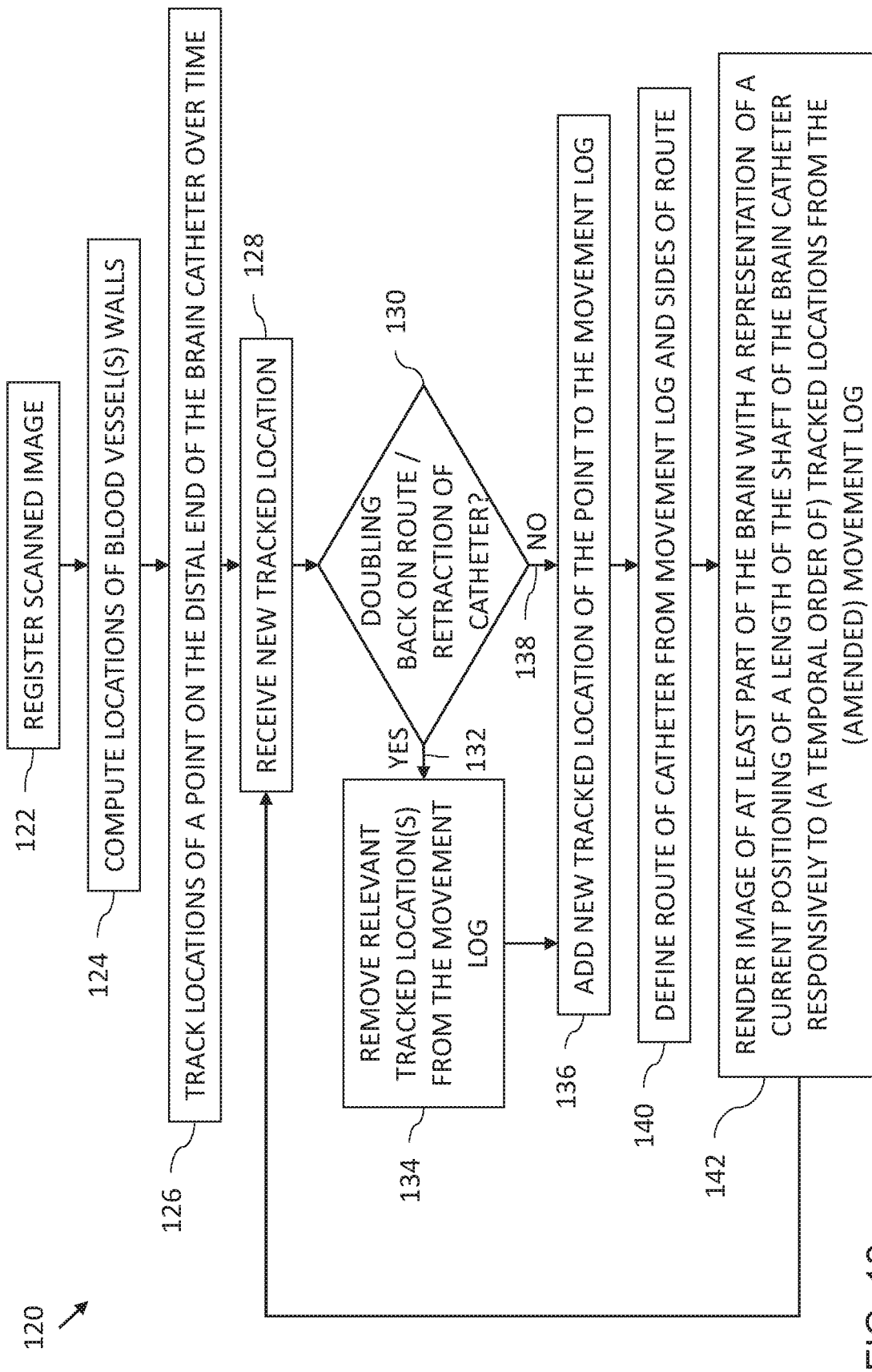
FIG. 12 is a flowchart including exemplary steps in a method of operation of the systems of FIGS. 1A and 1B.

Reference is now made to FIG. 12, which is a flowchart 120 including exemplary steps in a method of operation of the systems 20a and 20b of FIGS. 1A and 1B.

The processing circuitry 40 (FIG. 1) is configured to register (block 122) a scanned image (e.g., an Angiogram CT) of at least part of the brain 72 (FIGS. 5-8) delineating the blood vessels 76 (FIGS. 5-11). The processing circuitry 40 may be configured to compute (block 124) locations of walls of the blood vessels 76 from data of the registered image.

The tracking subsystem 33 (FIG. 1) is configured to track (block 126) locations of a point of the distal end of the brain catheter 28 (FIGS. 5A-B) over time responsively to a signal output by the location tracking transducer 62. The locations may be sampled by the tracking subsystem 33 periodically.

The processing circuitry 40 is configured to receive (block 128) a new tracked location of the point of the distal end of the brain catheter 28. It should be noted that not all received tracked locations are necessarily acted upon and used in further computations and/or decision making. For example, if a newly received tracked location is not spatially far enough from a most recent tracked location stored in the movement log 98 (FIGS. 9-11), the newly received tracked location may be discarded.

In a decision block 130, the processing circuitry 40 is configured to confirm whether, or not, the brain catheter 28 has been retracted in the blood vessel(s) 76 with respect to at least one tracked location already in the movement log 98 (FIGS. 9-11) responsively to at least the point of the distal end of the brain catheter 28 doubling back on the route 102 (FIGS. 9-11) defined by at least some of the tracked locations included in the movement log 98.

If the processing circuitry 40 confirms (branch 132) that the point of the distal end of the brain catheter 28 was retracted in the blood vessel(s) 76 with respect to one or more tracked locations included in the movement log 98 (FIGS. 9-11), the processing circuitry is configured to remove (block 134) the one or more tracked locations from the movement log 98 yielding an amended movement log 98.

Processing then continues with the step of block 136.

If the processing circuitry 40 does not confirm (branch 138) that the point of the distal end of the brain catheter 28 was retracted, the step of block 134 is skipped and then processing continues with the step of block 136.

The processing circuitry 40 is configured (block 136) to add the new tracked location of the point of the distal end to the movement log 98.

The processing circuitry 40 is configured to define (block 140) the route 102 by the tracked locations currently included in the movement log 98. The processing circuitry 40 is also configured to define the sides 112 (FIGS. 9-11) of the route 102. The route 102 is defined as an elongated volume, defined by the blood vessel walls or a given radius around the line 106 (FIGS. 9-11) joining the tracked locations in the movement log 98. The end of the route corresponding with the distal tip of the brain catheter 28 may be defined by a plane perpendicular to the line 106, or perpendicular to a center line defined by the walls of the blood vessel 76, at the point of the most recently tracked location in the movement log 98. In some embodiments, the processing circuitry 40 is configured to define the sides 112 of the route 102 based on at least a given radius around the line 106 connecting the tracked locations in the movement log 98. In other embodiments, the processing circuitry 40 is configured to define the sides 112 of the route 102 as being bound by walls of the blood vessel(s) 76.

The processing circuitry 40 is configured to render (block 142) to the display 56 (FIG. 1) the image 108 (FIGS. 9-11) of at least part of the brain of the living subject with the representation 100 of a length of the shaft of the brain catheter 28 in at least one blood vessel of the blood vessels 76 (FIGS. 5-11) of the brain with respective positions along the length of the shaft being located in the image 108 responsively to respective ones of the tracked locations from the movement log 98, which has been amended to add one or more tracked locations and optionally amended to remove one or more tracked locations as described in the step of block 134.

In some embodiments, the processing circuitry 40 is configured render the representation of the length of the shaft so that the respective positions along the length of the shaft are located in the image 108 responsively to the respective tracked locations according to a temporal order of the tracked locations in the movement log 98 with the position of the length of the shaft closest to the distal tip of the brain catheter 28 corresponding with a most recent one of the tracked locations in the amended movement log.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and subcombinations of the various features described hereinabove, as well as variations and modifications thereof which would occur to persons skilled in the art upon reading the foregoing description and which are not disclosed in the prior art.

What is claimed is:

1. A medical tracking system, comprising:
a catheter configured to be inserted into, and moved around in, blood vessels of a body-part of a living subject, and comprising a flexible shaft having a deflectable distal end, and a location tracking transducer in the distal end, the location tracking transducer being configured to output a signal that is indicative of a location of the transducer in the body-part;
a tracking subsystem configured to track locations of the distal end of the catheter over time responsively to the signal;
a display; and
processing circuitry configured to:
add the tracked locations of the distal end to a movement log;
render to the display an image of at least part of the body-part of the living subject with a representation of a length of the shaft of the catheter in at least one blood vessel of the blood vessels of the body-part, with respective positions along the length of the shaft being located in the image responsively to respective ones of the tracked locations from the movement log;
define sides of a route traveled by the catheter based on at least a given radius around a line connecting the at least some tracked locations;
in response to the catheter being retracted in the at least one blood vessel with respect to at least one tracked location, remove the at least one tracked location from the movement log yielding an amended movement log; and
render to the display the representation of the length of the shaft according to the amended movement log.

2. The system according to claim 1, wherein the processing circuitry is configured to render the length of the shaft so that the respective positions along the length of the shaft are located in the image responsively to the respective tracked locations according to a temporal order of the tracked locations in the movement log with one of the positions of the length of the shaft closest to a distal tip of the catheter corresponding with a most recent one of the tracked locations in the movement log.

3. The system according to claim 1, wherein the processing circuitry is configured to confirm that the catheter has been retracted in the at least one blood vessel with respect to the at least one tracked location responsively to at least the distal end doubling back on the route defined by at least some of the tracked locations included in the movement log.

4. The system according to claim 3, wherein the processing circuitry is configured to:
register a scanned image of at least part of the body-part delineating the blood vessels; and
compute locations of walls of the at least one blood vessel from data of the registered image.

5. The system according to claim 1, wherein the catheter has a diameter of 1 mm or less.

6. The system according to claim 1, wherein the tracking subsystem includes a location pad having at least one magnetic field radiator configured to transmit alternating magnetic fields into a region where the body-part is located, the location tracking transducer including a coil to detect at least part of the transmitted alternating magnetic fields.

7. The system according to claim 1, the processing circuitry being further configured to determine whether the movement log is indicative of the catheter doubling back on itself.

8. The system according to claim 7, the processing circuitry being further configured to, responsive to determining that the movement log is indicative of the catheter doubling back on itself, remove relevant tracked locations from the movement log.

9. A medical tracking method, comprising:
tracking locations of a deflectable distal end of a flexible shaft of a catheter configured to be inserted into, and moved around in, blood vessels of a body-part of a living subject over time responsively to a signal output by a location tracking transducer, the signal being indicative of a location of the location tracking transducer in the body-part;
adding the tracked locations of the distal end to a movement log;
rendering to a display an image of at least part of the body-part of the living subject with a representation of a length of the shaft of the catheter in at least one blood vessel of the body-part, with respective positions along the length of the shaft being located in the image responsively to respective ones of the tracked locations from the movement log;
defining sides of a route traveled by the catheter based on at least a given radius around a line connecting the at least some tracked locations; and
in response to the catheter being retracted in the at least one blood vessel with respect to at least one tracked location, removing the at least one tracked location from the movement log yielding an amended movement log; and
rendering to the display the representation of the length of the shaft according to the amended movement log.

10. The method according to claim 9, wherein the rendering includes rendering the length of the shaft so that the respective positions along the length of the shaft are located in the image responsively to the respective tracked locations according to a temporal order of the tracked locations in the movement log with one of the positions of the length of the shaft closest to a distal tip of the catheter corresponding with a most recent one of the tracked locations in the movement log.

11. The method according to claim 9, further comprising confirming that the catheter has been retracted in the at least one blood vessel with respect to the at least one tracked location responsively to at least the distal end doubling back on a route defined by at least some of the tracked locations included in the movement log.

12. The method according to claim 11, further comprising:
registering a scanned image of at least part of the body-part delineating the blood vessels; and
computing locations of walls of the at least one blood vessel from data of the registered image.

13. The method according to claim 9, wherein the catheter has a diameter of 1 mm or less.

14. The method according to claim 9, further comprising:
transmitting alternating magnetic fields into a region where the body-part is located; and
detecting at least part of the transmitted alternating magnetic fields by a coil location tracking transducer comprised in the catheter.

15. A software product, comprising a non-transient computer-readable medium in which program instructions are stored, which instructions, when read by a central processing unit (CPU), cause the CPU to:
track locations of a deflectable distal end of a flexible shaft of a catheter configured to be inserted into, and moved around in, blood vessels of a body-part of a living subject over time responsively to a signal output by a location tracking transducer, the signal being indicative of a location of the location tracking transducer in the body-part;
add the tracked locations of the distal end to a movement log;

render to a display an image of at least part of the body-part of the living subject with a representation of a length of the shaft of the catheter in at least one blood vessel of the body-part, with respective positions along the length of the shaft being located in the image responsively to respective ones of the tracked locations from the movement log; and define sides of a route traveled by the catheter based on at least a given radius around a line connecting the at least some tracked locations;

in response to the catheter being retracted in the at least one blood vessel with respect to at least one tracked location, remove the at least one tracked location from the movement log yielding an amended movement log; and render to the display the representation of the length of the shaft according to the amended movement log.

\* \* \* \* \*